United States Patent [19]

Argentar

[11] 4,284,551
[45] Aug. 18, 1981

[54] TERTIARY AROMATIC AMINE ACCELERATORS DERIVED FROM PARA-AMINOPHENETHANOL

[75] Inventor: Harold Argentar, Rockville, Md.

[73] Assignee: American Dental Association Health Foundation, Washington, D.C.

[21] Appl. No.: 98,886

[22] Filed: Nov. 30, 1979

[51] Int. Cl.$^3$ .......................... C08K 5/18; C08F 2/44; C08G 63/46
[52] U.S. Cl. .................... 260/42.43; 525/25; 525/112; 525/113; 525/217; 525/329; 525/379; 525/380; 526/220; 528/274; 433/228
[58] Field of Search ............... 525/112, 113, 217, 329, 525/379, 380; 526/220; 260/42.43; 528/274

[56] References Cited

U.S. PATENT DOCUMENTS

| | | | |
|---|---|---|---|
| 2,558,139 | 6/1951 | Knock et al. | 260/45.5 |
| 3,525,725 | 8/1970 | Kramer et al. | 260/88.7 |
| 3,541,068 | 11/1970 | Taylor | 260/41 |
| 3,594,354 | 7/1971 | Hazen et al. | 260/78.5 |
| 3,629,220 | 12/1971 | Sanchez | 260/92.8 |
| 3,631,009 | 12/1971 | Meyer | 260/82.3 |
| 3,631,069 | 12/1971 | Renner et al. | 260/326.3 |
| 3,634,379 | 1/1972 | Hauser | 260/89.5 |
| 3,682,875 | 8/1972 | O'Sallivan et al. | 260/89.5 R |
| 3,740,850 | 6/1973 | Brown et al. | 260/32.8 EP |
| 3,790,541 | 2/1974 | Langer, Jr. | 260/88.2 C |
| 3,966,573 | 6/1976 | Beam | 204/159.23 |
| 4,201,848 | 5/1980 | Kotani et al. | 525/314 |

FOREIGN PATENT DOCUMENTS 760351 5/1951 Fed. Rep. of Germany.

OTHER PUBLICATIONS

Brauer, Davenport & Hansen, 34 "Mod. Plast." p. 153 (1956), Accelerating Effect of Amines on Polymerization of Methyl Methacrylate.
Argentar, 80A "J. Res. Nat. Bur. Stand. (U.S.)", p. 173, (1976), Structure-and Solvent-Property Relationships for the Electronic Energies of Charge-Transfer Complexes Between Certain Benzene Derivatives.
Bowen & Argentar, 51 "J. Dent. Res." 473, (1972), Tertiary Aromatic Amine Accelerators With Molecular Weights Above 400.
Mleziva, 15 "Chem. Prum.", 80, (1965), Vliv Struktury Terc. Aromatickvchaminu Na Vytvrzovani Nenasycenych Polyesterovych Pryskyric.
Mleziva, 1 "Plast. Hmoty. Kauc.", 225, (1964), Vliv Aromatickych Aminu Na Rychlost Vytvrzovani Nenasycenych Polyesterovych Pryskyric.
Bowen & Argentar, 50 "J. Dent. Res." 923, (1971), Amine Accelerators for Methacrylate Resin Systems.
Schleyer et al., "Tetrahedron Letters", No. 14, pp. 1–7, (1959), Hydrogen Bonding in $\beta$-Aryl Ethanols, 3- and 4-Dimethylaminobenzyl Acrylate and Methacrylate and their Polymers.
Hrabak et al., "Makromol. Chem.", No. 179, pp. 2593–2601, (1978).
"Guide to Dental Materials and Devices", Chapter XII, Restorative Resins 7th Ed., 1974–1975, pp. 113–120.
"Guide to Dental Materials and Devices", Chapter XII Restorative Resins 6th Ed., 1972–1973, p. 112.
Lal & Green, "Journal of Polymer Science", vol. XVII, pp. 403–409, (1955).
F. Peyton & R. Craig, "Restorative Dental Materials", 4th Ed., p. 441, (1971).
P. Phillips, "Skinner's Science of Dental Materials", 7th Ed., pp. 193–194, 219–220, (1973).
Bowen & Argentar, 75 "J. Dent. Res.", 918, (1967), Diminishing Discoloration in Methacrylate Accelerator Systems.

Primary Examiner—Carman J. Seccuro
Attorney, Agent, or Firm—Allegretti, Newitt, Witcoff & McAndrews

[57] ABSTRACT

Tertiary aromatic amines derived from para-aminophenethanol act as accelerators for the peroxide catalyzed polymerization of vinyl monomers, especially methacrylates and acrylates, and for the curing of unsaturated polyesters. The amines are characterized by generally high reactivity and low toxicity, and by their yielding polymers of high strength and low color, and are thereby particularly suited for use in polymerizable or curable formulations employed in the filling and restoration of human teeth, in the preparation of cold-curing denture base materials for fabricating or repairing dentures and in the cementing of bone.

12 Claims, No Drawings

TERTIARY AROMATIC AMINE ACCELERATORS DERIVED FROM PARA-AMINOPHENETHANOL

BACKGROUND OF THE INVENTION

Field of the Invention

The invention described herein was made in the course of work under a grant or award from the Department of Health, Education and Welfare.

This invention relates to certain tertiary aromatic amines which are unique in their application as accelerators for the peroxide catalyzed polymerization of vinyl monomers and curing of unsaturated polyesters. The tertiary aromatic amine accelerators of the present invention are derived from para-aminophenethanol. The polymerized acrylic resin compositions are particularly useful in dentistry as improved restorative materials, with or without the addition of reinforcing fillers, and in medicine as orthopedic bone cements.

The structure of the lowest homolog of the tertiary aromatic amines employed in the instant invention, para-dimethylaminophenethanol, has been reported in the literature. Schleyer, Wintner, Trifan and Bacskai, 14 Tetrahedron Letters 1–7 (1959). Some loosely related compounds of the class of p-(1-pyrryl)-phenethyl alcohols have been employed in the healing arts because of their medicinal properties, inter alia, as analgesics, antiphlogistics and antipyretics. See U.S. Pat. No. 3,631,069; German Pat. No. 1,921,653. The reactivity of para-dimethylaminobenzyl alcohol, acetate, acrylate and methacrylate as accelerators for peroxide-catalyzed polymerization is discussed in Hrabak, Hynkova & Pivcova, 179 Makromol. Chem. 2593–601 (1978), and is there shown to be inferior to the commonly employed N,N-dimethyl-p-toluidine.

The use of other selected amines, especially simple amines, in conjunction with peroxides to bring about polymerization of acrylic resins has been known since 1940 or earlier. See German Pat. No. 760,351 to E. Schnebel. Certain acrylic resin/peroxide/aromatic amine polymerization systems have been employed in the past in the dental and medical arts. See for example, Guide to Dental Materials and Devices 113 (7th ed. 1974-75); Guide to Dental Materials and Devices 112 (6th ed. 1972-73); Lal & Green, 17 J. Polym. Sci. 403 (1955); F. Peyton & R. Craig, Restorative Dental Materials 441 (4th ed. 1971); R. Phillips, Skinner's Science of Dental Materials 193-94, 219-20 (7th ed. 1973); U.S. Pat. No. 2,558,139. A peroxide-free system is shown in U.S. Pat. No. 3,541,068. Tertiary amines with an aniline skeleton and higher molecular weight nitrogen substituents are suggested for use in dental materials in U.S. Pat. No. 3,740,850; Bowen & Argentar, 50 J. Dent. Res. 923 (1971); and Bowen & Argentar, 51 J. Dent. Res. 473 (1972). The use of tertiary amines as accelerators in conjunction with ethylenically unsaturated monomers and catalysts in other technological areas, such as in the areas of ink vehicles, wax compositions, metal adhesives, coatings and anaerobic sealants, is shown in U.S. Pat. No. 3,966,573; 3,790,541; 3,629,220; 3,634,379; 3,594,354 and 3,682,875. See also Mleziva, 15 Chem. Prum. 80 (1965); Mleziva, 1 Plast. Hmoty. Kauc. 225 (1964); U.S. Pat. Nos. 3,631,009; 3,525,725.

However, as has been documented in the literature, the aromatic amines previously used for acceleration of the peroxide catalyzed polymerization of acrylic resins have been characterized by a number of major disadvantages with respect to their use especially in dental materials. Some fail to cause rapid hardening at room temperature, a necessary property for a resin composition which is to be employed in medical or dental work. A number result in composites with poor resistance to mechanical wear, which is a serious drawback in a dental material which will be subjected to the pressures of chewing and grinding.

In general, the amines used previously have tended to introduce undesirable coloration into the dental material upon initiation of polymerization. See Bowen & Argentar, 51 J. Dent. Res. 473 (1972); Bowen & Argentar, 50 J. Dent. Res. 923 (1971); Bowen & Argentar, 75 J. Amer. Dent. Assn. 918 (1967); Brauer, Davenport & Hansen, 34 Mod. Plast. 153 (1956). Prior art accelerators have also exhibited lack of color stability upon exposure of the specimen containing the compound to either visible or near-visible ultraviolet light (such as sunlight) over a period of time. Such exposure would occur as a matter of course for resin compositions employed as dental materials. Since the cosmetic appearance of restorative dental work is very important to the patient, these difficulties are of considerable concern in the field of dentistry.

Furthermore, it is suspected that, because of their toxicity, aromatic amines are involved in eliciting an unfavorable dental pulp response to the final polymerized resin composition. See Bowen & Argentar, 51 J. Dent. Res. 473 (1972); U.S. Pat. No. 3,740,850. The toxicity of the amines to surrounding tissues would also be an important consideration in choice of orthopedic bone cements.

See also applicant's copending application Ser. No. 885,275, filed Mar. 10, 1978, for a discussion of different classes of amine accelerators.

SUMMARY OF THE INVENTION

The psychological importance to the patient of the appearance of restorations or billings in teeth, and practical importance of decreased need for replacement, make reduced discoloration tendency and dental pulp irritation coupled with high mechanical strength of key importance in dental restorative resin formulations. An aromatic amine that is very reactive could be employed to bring about polymerization or curing of vinyl monomers or unsaturated polyesters within an acceptable time period in a concentration much lower than that required for other amines. If the tendency toward amine discoloration and toxicity is not related to the reactivity of the amine with peroxides, then the discoloration tendency and possible pulp irritation of a resin restorative formulation containing an especially reactive amine in the reduced quantity required would accordingly be reduced in comparison to those formulations containing other amines.

It has now been found that the nitrogen substituents play less of a role in governing the behavior of a tertiary aromatic amine than do the aromatic substituents, and that a correlation of the reactivity of aromatic amines (for amines at the same initial molar concentration) possessing the same nitrogen substituents with the electron-donating abilities of the variable aryl substituents as measured by the total $\sigma^+$ value of the substituents(s) indicates that a $\sigma^+$ value for the ring substituent(s) of between $-0.05$ and $-0.40$, preferably approximately $-0.20$, is optimal. This correlation is useful primarily with respect to meta- and para- substituents. The definition of $\sigma^+$ and examples of its use for correlating certain properties of aromatic amines as given in Argentar, 80A *J. Res. Nat. Bur. Stand.* (U.S.) 178 (1976), is incorporated herein by reference. The invention here described makes use of a polymerization system containing a class of tertiary aromatic amines possessing ring substituents with approximately this characteristic $\sigma^+$ value.

The tertiary aromatic amines forming a part of the present invention are derived from para-aminophenethanol and are selected from the following:

(A)
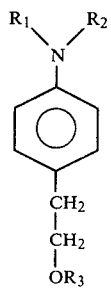

where $R_1$ and $R_2$ are the same or different and are selected from the following groups:
(a) —$CH_3$,
(b) —$CH_2CH_2\ C_nH_{2n+1}$ with n varying between 0 and 18, (c)
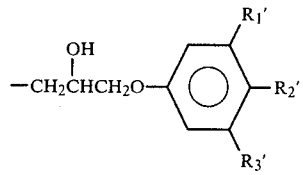

where $R_1'$, $R_2'$ and $R_3'$ are each either hydrogen, normal alkyl, —$C_nH_{2n+1}$, with n varying between 1 and 20, or t-butyl, but if one R' is t-butyl, then the adjacent R' is hydrogen, (d)
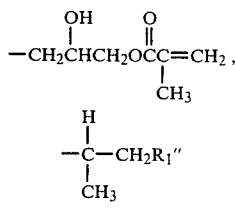

where $R_1''$ is —$C_nH_{2n+1}$ with n varying from 0 to 17, or
(f) —$CH_2CH_2OH$;
and where $R_3$ is either hydrogen, or a lower normal alkanoyl group,

with n varying between 1 and 20, or

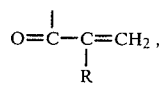

where R is hydrogen or a methyl group; or (B) a polymeric amine having 10 or fewer amine groups which is the reaction product of the amine

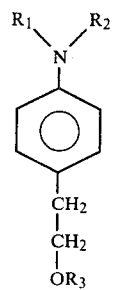

in which $R_1$ and $R_2$ are each hydrogen and $R_3$ is as defined in (A) with the diglycidyl ether of bisphenol A, viz.,

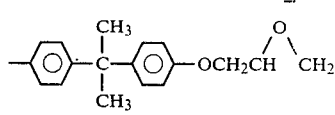

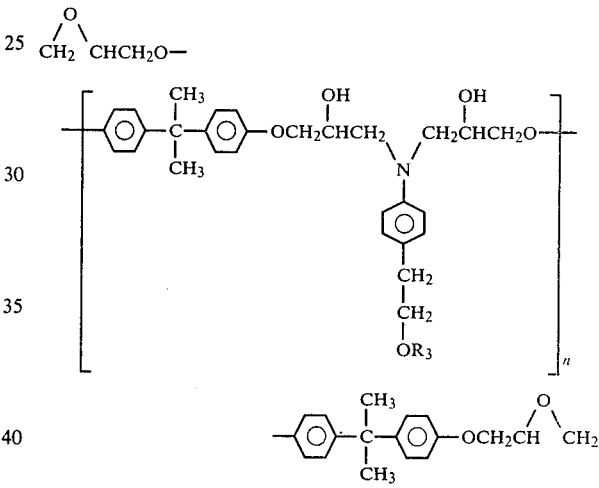

where n varies between 1 and 10, or the hydrolysis product of this polymeric amine, viz.,

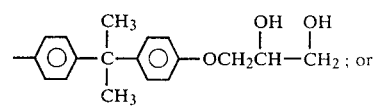

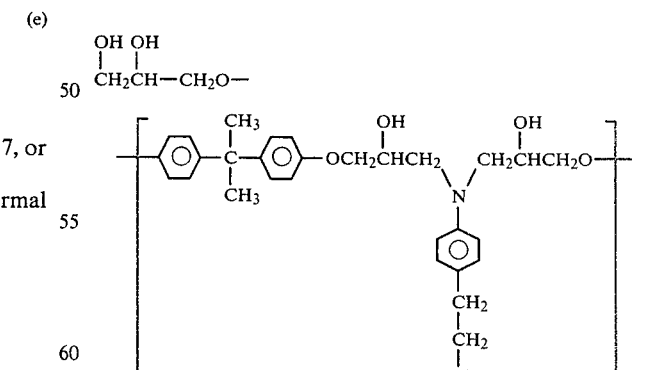

(C) an amine having the formula

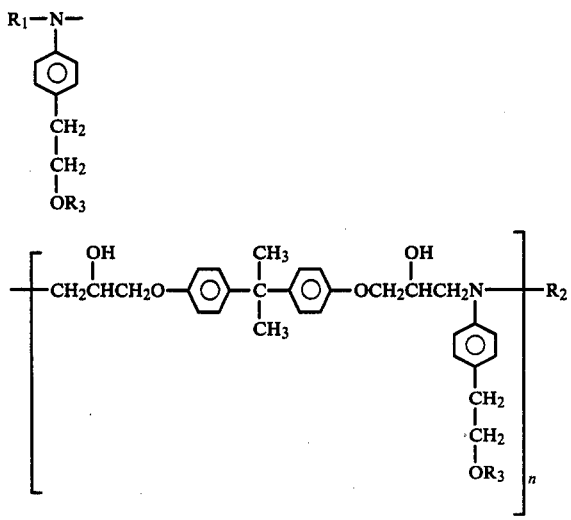

with n varying between 1 and 10, where $R_1$ and $R_2$ are as defined in (A) or are of the formula

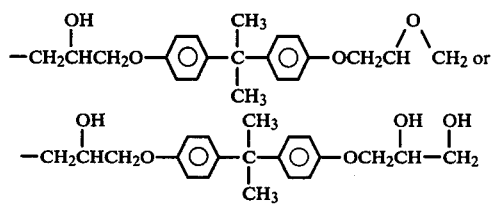

and where $R_3$ is as defined in (A); or (D) a polymeric amine having 10 or fewer amine groups which is the reaction product of the amine (B) with methacrylic or acrylic acid; or (E) an amine having the formula

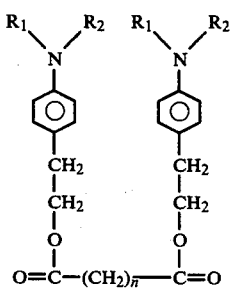

where $R_1$ and $R_2$ are as defined in (A) but with no greater than 5 carbon atoms in the alkyl substituents of $R_1$ and $R_2$, and where n varies between 2 and 10; or (F) an amine having the formula

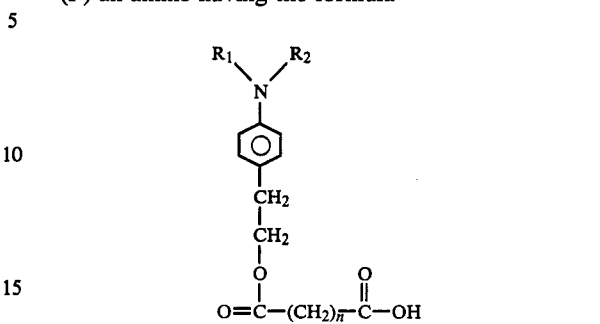

where $R_1$ and $R_2$ are as defined in (A), and where n varies between 2 and 10.

In general, the invention involves these tertiary aromatic amines, in most instances believed novel in their own right, and their use as polymerization or curing accelerators in the peroxide catalyzed polymerization of vinyl monomers or curing of unsaturated polyesters. In a preferred form of the invention, the tertiary aromatic amines are employed in a restorative dental material, in a cold-curing denture base material for fabricating or repairing dentures or in a bone cement comprising a methacrylate ester, a diacyl peroxide catalyst and the amine. Particularly when employed in a method of treating human teeth for filling and for restorative purposes, the amine-containing composition contacted with the teeth may further comprise a reinforcing filler of the type routinely used in the dental field.

DETAILED DESCRIPTION OF THE INVENTION

The tertiary aromatic amines employed in the present invention may be used individually or in combination. The total accelerator concentration should be sufficient to accelerate catalysis, and will preferably fall within the range of 0.1 to 2.0% by weight of the entire polymerizable or curable mass.

While the definitions of these tertiary aromatic amines are believed self-explanatory, formulas for representative compounds will be provided to aid in their visualization. An example of a derivative of type (C) is the following:

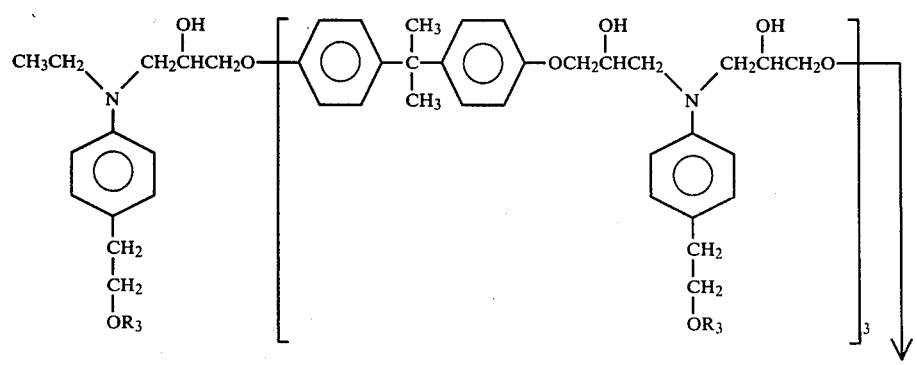

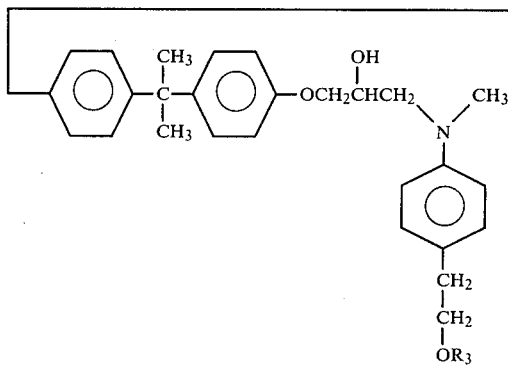

In this instance, $R_1=CH_2CH_3$ and $R_2=CH_3$.

An example of derivative of type (D), in which the acid reactant is methacrylic acid, is:

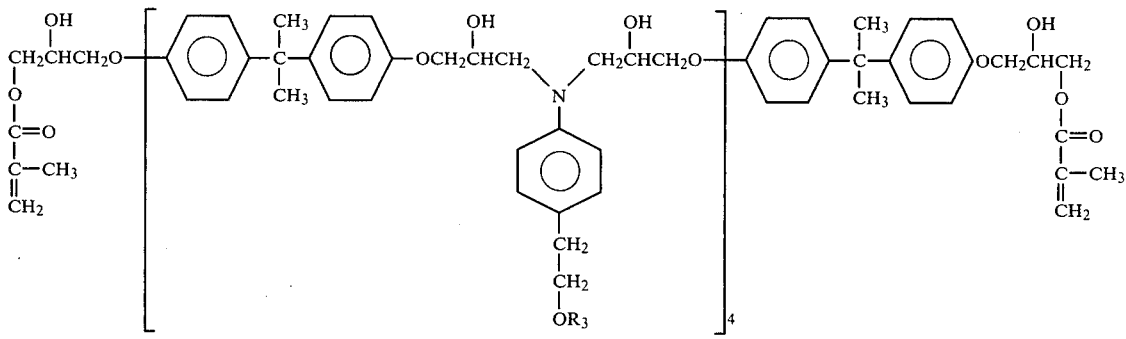

The vinyl monomers polymerized in the practice of the present invention may include, at any one time, either a single type of monomer or a mixture of monomers. Preferred monomers are the various esters of methacrylic acid and acrylic acid. Similarly, one or more unsaturated polyesters may be included at any one time. Suitable polyesters include, e.g., those derived from maleic acid. Additionally, a mixture of vinyl monomers and unsaturated polyesters may be simultaneously polymerized and cured. The preferred monomers for use in dental applications are the methacrylates, and primarily the dimethacrylates. The acrylate esters may tend to be somewhat more toxic than the methacrylate esters.

Suitable initiators for the free-radical polymerization of these monomers or for curing of the polyesters are the peroxides, especially the diacyl peroxides, and in particular lauroyl and benzoyl peroxide. The catalysts may be employed alone or in mixtures with one another. Any suitable amount of the initiator may be used, but in general a satisfactory catalyst concentration falls within the range of 0.1 to 2.0 percent by weight of the entire polymerizable mass.

Reinforcing fillers are employed as a component of the polymerizable or curable mass in certain applications of the invention, especially in the preparation of restorative dental materials. Many such fillers for dental materials are known in the art; any appropriate filler which improves the characteristics of the formulation may be utilized. At present, a preferred reinforcing filler is fused silica in conjunction with a silane keying agent.

In some instances, it may also be desirable to include a polymerization inhibitor or a stabilizing agent such as butylated hydroxytoluene (BHT) in the polymerizable or curable mass in order to prevent premature polymerization of the composition prior to its use. Incorporation of ultaviolet absorber(s) may be necessary for complete color stability of the polymer against the effect of light or ultraviolet radiation. For specific purposes, coloring agents may also be incorporated.

The following Examples illustrate the preparation, use and comparative evaluation of a number of the tertiary aromatic amines of the instant invention.

EXAMPLE I

Synthesis of Para-dimethylaminophenethanol

Para-dimethylaminophenethanol is synthesized using the following reaction:

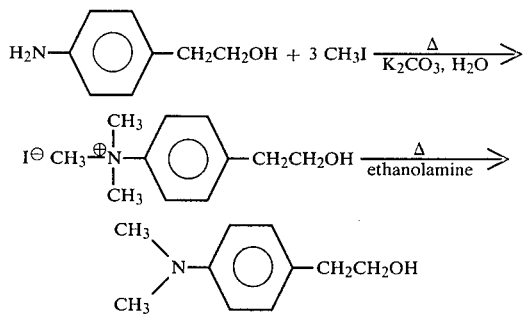

The final compound is obtained in a 64% overall yield and has a melting point of 52°–53° C.

EXAMPLE II

The above synthesis is repeated except that the quartenary acetate salt instead of the iodide is initially synthesized. Two fractions are found: one is a translucent yellow liquid, the other a crystalline white solid. After structural characterization using infra-red and nuclear magnetic resonance spectrometric techniques, the white solid is identified as p-dimethylaminophenethanol, while the identity of the yellow liquid is not ascertained, although there is some indication that it is a tertiary aromatic amine containing an aldehyde group.

EXAMPLE III

Testing of Para-dimethylaminophenethanol and Comparison With Other Accelerators Composites are made using a powder-liquid system. The liquid component contains:

70% bis(3 methacryloxy-2-hydroxypropyl)bisphenol-A, commonly referred to as "Bis-GMA", which is the monomer;

30% triethylene glycol dimethacrylate (TEGDMA) as the diluent monomer (used to decrease the viscosity of Bis-GMA). To this monomer solution is added:

0.2% butylated hydroxytoluene (BHT), as an inhibitor, and;

varying amounts of tertiary aromatic amine accelerator.

The silanized powder is made up of spherical silica (procured from Corning Glass) and barium fluoride-containing glass coated with 1% benzoyl peroxide. (The function of the glass in the composite system is to decrease thermal expansion and curing shrinkage and to modify the mechanical properties of the cured material. Temperatures in the mouth range from 5° C. to about 55° C. Without the presence of glass, the material would expand and contract with changes in temperature to such a degree that it would be less practical for use as a dental restorative material. When the composite contracts, it pulls away from the cavity walls, allowing food and bacteria to enter into the resulting voids, leading to secondary caries and necessitating eventual replacement of the filling.)

The composites were tested for setting time, diametral tensile strength, compressive strength and color stability by the following test procedures:

Setting Time

The test method described below is based on American Dental Association specification no. 8 for zinc phosphate cement.

To determine setting time, a brass ring approximately 4.8 mm high and 9.5 mm internal diameter is placed on a glass plate and filled with composite material. Within 2 minutes after starting the mix the specimen is transferred to a 37° C., 100% relative humidity water bath. This is designed to simulate the environment of the mouth. Two and one half minutes after starting the mix, a standard Gillmore needle, weighing 454 gm and having a flat end 1.06 mm in diameter is carefully lowered onto the horizontal surface of the composite. This is repeated at thirty second intervals until setting has occurred. The time of setting is the number of minutes elapsed from the starting of the mix to the time when the needle, under the force of its own weight, does not leave an impression on the surface of the composite.

American Dental Association specifications require that the setting time of composites be within a 2–8 minute range in order to be considered clinically acceptable.

Diametral Tensile Strength

The test was conducted according to American Dental Association specification No. 27 for Direct Filling Resins.

Five test specimens are made, using a 3:1 powder: liquid ratio. This is the ratio used for all tests of this material. The components are mixed on a waxed mixing pad with a spatula made of agate, or some other non-reactive material. The composite is mixed for 90 seconds, after which it is transferred to a mold with dimensions 3 mm×6 mm. The mold is sandwiched between two glass plates and placed in the water bath for 15 minutes. Upon being removed from the bath, the specimens are polished with 200 mesh silicon carbide powder and water. The molds containing the specimen are drawn back and forth across a glass plate coated with the abrasive and water. They are then numbered and ejected from the mold. The five specimens are placed together in a dish of distilled water and placed in the water bath for 24 hours. After removal from the bath, the specimens' width and diameter are measured to the nearest ten-thousandth of an inch. They are then placed, vertically, between the parallel platens of a Universal testing machine. A small piece of blotting paper wet with water is inserted between the specimen and platens of the testing machine. The specimen is then loaded at the rate of 0.4 cm/second until breaking.

The breaking load and dimensions are fed into the computer and results are given in megapascals (MPa) (a metric unit equalling 145 psi). American Dental Association specifications require a tensile strength of at least 34 MPa.

Compressive Strength

The procedure for compressive strength testing is identical to that for tensile strength testing, except that the specimens are placed horizontally on the Universal Instron and loaded at the rate of 0.2 inches per minute. Compressive strength results are generally much higher (four to five times higher) than tensile strength results.

Color Stability

Two specimens are made using stainless steel molds 20.0±0.1 mm in diameter by 1.0±0.05 mm in thickness. These samples are soaked for 24 hours in a water bath, as before, but are not polished.

When they are removed from the bath, foil is placed over half of each specimen. The specimen is positioned 5 mm above the surface of an aluminum turntable with its center 60 mm from the center of the turntable. The specimen is exposed to the UV radiation of a Westinghouse 275 watt RS sunlamp. The height of the lamp above the specimen is such that, with a Blak-Ray J-221 Long Wave UV Meter sensor resting on the turntable at the specimen level, the ultraviolet radiation is 1700±100 micro-watts per $cm^2$. The radiation is metered immediately before and after each test to insure that the radiation of the lamp remains within tolerance throughout the exposure. The specimens are then rotated at $33\frac{1}{3}$ rpm for 24 hours.

Following a 15 minute cool-down period, the samples are removed from the table. The foil is removed from the unexposed half of each specimen and each is given a subjective rating, 1 being little or no color change and 4 being a dramatic amount of color change. This rating is administered by three or four individuals and an average is taken.

Results

Para-dimethylaminophenethanol solutions are made in concentrations of 20, 28, and 36 mg per 10 grams monomeric solution, and subjected to the above-described regimen of tests. The results are set forth in Table 1. Comparative data for a commonly used commercial composite and an experimental composite using a different class of accelerator are given in Tables 2 and 3.

TABLE 1

Test Results for p-Dimethylaminophenethanol

| Concentration of Amine in liquid, % | Setting Time min. | Tensile Strength MPa | Compressive Strength MPa | Color Stability* |
|---|---|---|---|---|
| 0.20 (12 mm)** | 3 | 51.1 ± 3.4*** | 266.7 ± 4.9*** | 2 |
| 0.28 (17 mm) | 2½ | 53.8 ± 1.7 | 280.6 ± 3.9 | — |
| 0.36 (22 mm) | 2 | 56.3 ± 2.1 | — | — |

*Color stability ranking: 1 = no visible change; 4 = large change
**Millimolal
***Standard Deviation

TABLE 2

Properties of a Commonly Used Commercial Composite*

| Setting Time min | Tensile Strength MPa | Compressive Strength MPa | Color Stability |
|---|---|---|---|
| 2–3 | 48.4 ± 2.6 | 203.1 ± 4.1 | 1.5 |

*Adaptic employing a paste-paste system.

TABLE 3

Properties of Composite Made From Powder-Liquid Components Containing Dimethyl-p-toluidine as Accelerator

| Amine Concentration % | Hardening Time min | Tensile Strength MPa | Compressive Strength MPa | Color Stability |
|---|---|---|---|---|
| 0.14 (10.2mm)* | 6.0 | 23.8 + 4.8 | 147.7 + 12.2 | 1.5 |
| 0.23 (17.0mm) | 4.5 | 44.8 + 1.7 | 194.4 + 3.6 | 3 |
| 0.28 (20.7mm) | 4.5 | 28.2 + 6.2 | 152.9 + 25.0 | — |
| 0.32 (23.7mm) | 1.5 | — | — | — |
| 0.60 (44.4mm) | 1.0–1.5 | — | — | — |
| 0.75 (55.5mm) | 4.0 | — | — | — |

*Millimolal

Discussion

Para-dimethylaminophenethanol shows potential as a clinically useful accelerator. It is highly reactive, as indicated by the setting times (Table 1). Under some conditions, the amine exhibits an increase in accelerating ability with time, as compared with most amines which merely maintain reactivity or show a decrease. Composites containing para-dimethylaminophenethanol, at optimum concentrations, give tensile strength values that are somewhat higher than those exhibited by the commercially used composite and the commonly employed dimethyl-p-toluidine-accelerated composite (see Tables 2 and 3). Compressive strength values are appreciably higher.

The color of the cured composite accelerated with the new amine is remarkably white, and its color stability rating of 2 is acceptable.

Based on the low toxicity of the new accelerator's analogues, this accelerator is predicted to contribute minimal toxicity to a composite.

The rapid setting times of composites containing p-dimethylaminophenethanol may have to be moderated in some instances by the use of a less reactive diluent monomer or by an increase in concentration of inhibitor (BHT).

EXAMPLE IV

Testing of Para-dimethylaminophenethanol and Comparison With Other Accelerators

Composites are prepared using a powder-liquid system, in which the powder to liquid ratio is three to one. The total ingredients in the powder-liquid system utilized are:

Components of Liquid 72.4% Bis-GMA;
27.6% 1,6-Hexamethylene glycol dimethacrylate (HGDMA) as a comonomer and as a diluent to reduce the high viscosity of Bis-GMA;
0.2% Butylated hydroxytoluene (BHT) as an inhibitor for polymerization and as a preservative to keep the liquid from polymerizing in storage;
Varying amounts of tertiary amine accelerator.

Components of Powder

Spherical radiopaque silica procured from Corning glass coated with silane;
1% peroxide coated on the surface of the powder.
Ultraviolet absorbers and pigments may also be added to improve the color and color stability.

Evaluating the Properties of Various Amines

The following amines were incorporated into composites and evaluated for setting time, tensile strength, compressive strength, color stability, and water sorption:

| Amine | Abbrev. | Source |
|---|---|---|
| N-N-Dimethyl-p-toluidine | DMPT | Commercial |
| 4-N,N-Dimethylamino-phenylacetic Acid | DMAPAA | Synthesized |
| N,N-Dimethyl-p-aminophenyl-propionic Acid | DMAPPA | Synthesized |
| N,N-Dimethyl-p-amino-phenethanol | DMAPE | Synthesized |

Setting Time

The procedure of Example 3 is employed, except that the specimen is transferred to the bath within three minutes after starting the mix, and the needle is first lowered three and one-half minutes after starting the mix. The setting time is determined twice for each sample, and if the deviation exceeds one minute, a third determination is made and the measurements averaged.

Diametral Tensile Strength

A small standard mix of material is placed in a stainless steel mold 2.5 mm high and 6 mm inside diameter which is resting on a glass plate. Another flat glass plate is placed on top of the mold and the plates are tightly clamped together. (If necessary, the stainless steel mold and glass plates are coated with a non-reactive lubricant to prevent the specimen from adhering. If a lubricant is used, the specimen is washed thoroughly in a mild detergent solution before it is placed in water for the 24 hour storage cycle). Two minutes from the start of the mix, the assembly is placed in an environment of 37°±1° C. and 95±5% relative humidity and allowed to remain for 15 minutes. The specimens and the mold are removed and the ends ground flat using 200 grit (or finer) silicon carbide and water. The specimen is ejected from the mold and stored in distilled water at 37°±1° C. for 24 hours. The specimen is then placed on its side between parallel platens of the testing machine. A small piece of blotting paper (approximately 0.5 mm thick) wet with water is inserted between the platens of the testing machine and each side of the specimen. The specimen is then loaded continuously in compression at 1 cm/min. to the breaking point. The strength is computed as follows:

$$T_s = \frac{2P}{\pi dl} \text{ units for } T_s = MN/m^2$$

where
P=load at fracture (kg)
d=diameter of specimen (cm)
l=length of specimen (cm)

The value for diametral tensile strength is reported as the average of three or more from a lot of five specimens and is rounded off to the nearest 0.1 meganewton per square meter (14.5 psi). If the values for individual specimens fall more than 15% above or below the average of the five, they are discarded and the average of the remaining specimens is reported. In case more than two of the specimens are eliminated, the test is repeated.

Compressive Strength

The test specimens are cylinders 2.5 mm high and 6 mm in diameter. The ends of the specimens are flat and smooth and are parallel to each other and at right angles to the long axis of the cylinder.

A cylindrical mold 12 mm high and 6 mm in diameter, made of hard rubber, glass, stainless steel or any other substance which will not react with the cement, is placed on a flat glass plate. The mold may be coated with a 3 percent solution of a microcrystalline wax (melting point 86°–91° C.) in benzene. It is slightly overfilled with cement of standard consistency within 3 minutes after commencing the mixing. A second flat glass plate is pressed on top of the mold. The mold and plates are held firmly together with a small C clamp. All apparatus is at room temperature. Three minutes after starting the mix, the mold and clamp are transferred to an atmosphere of 100 percent relative humidity at 37° C. One hour later the ends of the cylinder are surfaced plane at right angles to the axis. The ends of the specimens may be ground flat by the use of a small amount of 200-mesh silicon carbide powder and water. The molds containing the specimens are drawn back and forth across a glass plate coated with the abrasive and water. They are rotated about one-fourth turn every few strokes. The test specimens are kept wet during the grinding.

After surfacing, the specimens are removed from the mold by a screw jack and immersed in distilled water at 37° C. The time lapse between the starting of the mixing and the crushing is 24 hours. A small piece of blotting paper (approximately 0.5 mm thick) wet with water is inserted between the ends of the specimen and the platens of the testing machine. The specimens are loaded at the rate of 0.5 cm/min and are kept wet during the test. The strength is computed as follows:

$$C_s = \frac{4P}{\pi d^2}$$

where
P=load at fracture (kg)
d=diameter of specimen (cm)

The value for compressive strength is reported as the average of three or more from a lot of five specimens and is rounded off to the nearest 10 kg/cm². If the values for individual specimens fall more than 15 percent below the average of the five, they are discarded and the average of the remaining specimens is reported. In case more then two of the specimens are eliminated, the test is repeated.

Color Stability

Color stability specimens are formed using a stainless steel ring having an inside diameter of 20±0.1 mm, and a thickness of 1±0.05 mm. The ring is placed on a flat glass plate and a specimen mix introduced into it. Another flat glass plate is used to press the material into the ring. (If necessary, the stainless steel ring and glass plates may be coated with a non-reactive lubricant to prevent the specimen from adhering. If a lubricant is used, the specimen is washed thoroughly in a mild detergent solution before it is placed in water for the 24 hour storage cycle). The plates are tightly clamped together so that the mold and glass plates are in contact. Two minutes after the mix is started, the assembly is placed in an environment of 37°±1° C. and 95±5% relative humidity for 15 minutes and then the specimen is removed from the mold. The specimen is washed with distilled water to remove any fragments from the surface and stored for 24 hours in distilled water at 37°±1° C. The surface of the specimen is then dried and one half of the specimen is exposed to the radiation of a lamp with a Westinghouse RS bulb which has been in use not less than 50 nor more than 400 hours. The light source is a combination tungsten filament mercury-arc enclosed in Corex D or other glass which has a low transmission below 2800 Å. The lamp is rated at 400 watts. The specimen is carried on an aluminum disc which is centered under the bulb and which rests on a turntable operated at 33 rpm. The specimen is held approximately 5 mm above the disc and 12.7 cm from the center and is maintained between 60° and 65° C. The plane of the top surface of the specimen is 17.8 cm from the bottom of the bulb. After exposure for 24 hours, the exposed half of each specimen is comared with its unexposed half. Two specimens are tested. The comparison is made by three people using a visual inspection in daylight on a white background and is recorded as the average of three subjective ratings, 4 indicating little or no color change and 1 indicating a drastic color change.

Water Sorption

A sample is placed in a stainless steel ring (inside diameter 20±0.1 mm and 1.0±0.05 mm thick) which is sitting on a flat glass plate. Another flat glass plate is used to press the material into the ring. Two minutes after the mix is started, this assembly is placed in an environment of 37°±1° C. and 95±5% relative humidity, and allowed to remain for 15 minutes. The specimen is then removed from the ring. All surfaces of the discs are clean and smooth, and the top and bottom are flat. (If the surfaces are not flat, due to excessive shrinkage of the material, specimens are formed in a ring 1.15 mm thick and reduced to the prescribed thickness using accepted wet grinding metallographic surface reduction procedures ending with abrasion against 600 grit silicon carbide). (If necessary, the stainless steel ring and glass plates may be coated with a non-reactive lubricant to prevent the specimen from adhering. If a lubricant is used, the specimen is washed thoroughly in a mild detergent solution before it is placed in the desiccator). The discs are dried in a desiccator containing dry anhydrous calcium sulfate ($CaSO_4$) or silica gel (freshly dried at 130° C.) at 37°±1° C. for 24 hours. The desiccator is then removed from the controlled temperature so that each sample can be weighed individually to a precision of 0.2 mg.

This cycle is repeated until constant weight is attained, that is, until the weight loss of each disc is not more than 0.05 mg in any 24 hour period. The discs are then immersed in distilled water at 37°±1° C. for 1 week (±2 hrs.), after which time the discs are removed from the water with forceps, blotted with a clean, dry cellulose towel until free from visible moisture, and waved in the air for 15 seconds. Weighing is completed 1 minute after removal of the specimen from the water.

The values for water sorption are calculated as follows for each disc:

$$\text{sorption (mg/cm}^2\text{)} = \frac{\text{wt. after immersion (mg)} - \text{conditioned wt. (mg)}}{\text{surface area (cm}^2\text{)}}$$

The average of the determined values for 3 discs is recorded. In some instances the samples are reused from color stability tests.

Results and Discussion

Results from tests show that the inventive amine produces composites with equal and, in some cases, better properties than commercial composites. An added advantage of these inventive composites over the commercial products is their predicted lower levels of toxicity.

DMAPE-19 mm and DMAPAA-19 mm produce the highest overall values. However, all of the amines tested give values exceeding American Dental Association specification requirements for a tensile strength not less than 34 MPa, water sorption less than 0.7 mg/cm$^2$, and a setting time between 2 and 8 minutes.

In addition, two additional tests are run. Five samples of DMPT-15 mm are left in the temperature-controlled water for 1 week instead of the usual 1 day. There is no significant change in compressive strength.

Tests are also run on samples of DMAPE-21 mm with an older batch of Bis-GMA. Any change of property at this concentration of DMAPE is also not significant statistically.

There appears to be no significant relationship between amine concentration and setting time. DMPT and DMAPPA do, however, reach a minimum at a 17 mm concentration. DMAPE and DMAPAA show no significant change in setting time at different concentrations.

Taking into account standard deviations, a definite significant relationship between amine concentrations and tensile strength cannot be reached on the basis of this set of experimental data. Since the tensile strength for composites with DMAPE appears to rise as the amine concentration is increased, a formulation containing a 21 mm concentration of the amine is also tested. The tensile strength of this composition shows a drastic decrease from the 19 mm concentration.

Many of the amines tested do exhibit a relationship between amine concentration and compressive strength. Formulations with DMPT, from 15 to 19 millimolals in the liquid, give a decrease in compressive strength with increasing amine concentration. On the other hand, with DMAPE the compressive strength consistently increases with concentration and, for that reason, a 21 mm concentration is evaluated. This concentration proves to have slightly lower values than composites containing 19 mm of the amine. For DMAPAA, compressive strength consistently increases but is not determined at 21 mm because of the lower tensile strength values at higher amine concentrations.

All of the amines exhibit good color stability varying from 3 to 4 on the arbitrary evaluation scale. It is likely that even more favorable results can be obtained if ultraviolet absorbers are added to the composites.

Preliminary data on water sorption show that all of the values are within American Dental Association requirements.

See Tables 4 and 5 for comparative data. Certain concentrations of DMAPE exhibit values comparable to commercially used dental composites.

TABLE 4

| | | | | | | Strength | | | | Water |
|---|---|---|---|---|---|---|---|---|---|---|
| Amine | | Concentration | | Setting | Tensile | | Compressive | | Color | Sorption |
| Name | M.W. | Molal | Wt. % | Time | PSI | MPa | PSI | MPa | Stability | (mg/cm$^2$) |
| DMPT | 135 | 15 mm | .20 | 4.5 min. | 6654 ± 609 | 45.89 ± 4.20 | 39984 ± 3215 | 275.76 ± 22.17 | 3.5 | 0.63 ± 0.01 |
| | 135 | 17 mm | .23 | 3.0 min. | 6240 ± 308 | 43.03 ± 2.62 | 35722 ± 1408 | 246.36 9.71 | 3.5 | 0.58 ± 0.00 |
| | 135 | 19 mm | .26 | 4.5 min. | 6905 ± 452 | 47.62 ± 3.12 | 35609 ± 2532 | 245.58 ± 17.46 | 3.5 | 0.56 ± 0.03 |
| | | AFTER 1 WEEK IN BATH: | | | | | | | | |
| | | 15 mm | .20 | 4.5 min. | | | 40276 ± 1348 | 277.77 ± 9.30 | | |
| DMAPE | 165 | 15 mm | .25 | 3.5 min. | 6684 ± 68 | 46.10 ± 0.47 | 37919 ± 3050 | 261.51 ± 21.03 | 3.5 | 0.53 ± 0.04 |
| | 165 | 17 mm | .28 | 3.0 min. | 6923 ± 380 | 47.74 ± 2.30 | 39293 ± 571 | 270.99 ± 3.94 | 3.0 | 0.55 ± 0.02 |
| | 165 | 19 mm | .31 | 3.0 min. | 7260 ± 355 | 50.07 ± 2.31 | +43728 ± 1630 | 301.57 ± 11.24 | 3.0 | [3] 0.89 ± 0.50 |
| | 165 | 21 mm[1] | .35 | 2.5 min. | 5739 ± 240 | 39.58 ± 1.65 | 41399 ± 636 | 285.51 ± 4.38 | 3.0 | [4] |

TABLE 4-continued
PROPERTIES OF COMPOSITES MADE WITH VARIOUS AMINE ACCELERATORS

| Amine | | Concentration | | Setting Time | Strength | | | | Color Stability | Water Sorption (mg/cm$^2$) |
|---|---|---|---|---|---|---|---|---|---|---|
| Name | M.W. | Molal | Wt. % | | Tensile | | Compressive | | | |
| | | | | | PSI | MPa | PSI | MPa | | |
| | 165 | 21 mm$^2$ | .35 | 3.0 min. | 5459 ± 307 | 37.65 ± 2.11 | 39403 ± 2619 | 271.74 ± 18.06 | 3.0 | 0.57 ± 0.04 |
| DMAPPA | 193 | 15 mm | .29 | 6.0 min. | 5995 ± 496 | 41.35 ± 3.42 | 34886 ± 1880 | 240.59 ± 12.96 | 3.0 | 0.55 ± 0.06 |
| | 193 | 17 mm | .33 | 4.0 min. | 6255 ± 514 | 43.14 ± 3.54 | 38190 ± 678 | 263.38 ± 4.68 | 4.0 | 0.55 ± 0.01 |
| | 193 | 19 mm | .37 | 5.0 min. | 6643 ± 606 | 45.82 ± 4.18 | 37381 ± 2884 | 257.80 ± 19.89 | 3.0 | 0.58 ± 0.02 |
| DMAPAA | 179 | 15 mm | .27 | 2.0 min. | 7567 ± 536 | 52.19 ± 3.70 | 40007 ± 25553 | 275.91 ± 17.61 | 3.0 | 0.56 ± 0.01 |
| | 179 | 17 mm | .30 | 2.5 min. | 7486 ± 380 | 51.63 ± 2.62 | 40384 ± 1591 | 278.51 ± 10.97 | 3.0 | [3]0.55 ± 0.01 |
| | 179 | 19 mm | .34 | 2.0 min. | 7276 ± 547 | 50.18 ± 3.77 | 42977 ± 949 | 296.40 ± 6.54 | 3.0 | 0.61 ± 0.06 |

[1]Made with same BIS-GMA batch.
[2]Made with 1976 Batch of BIS-GMA.
[3]Not final results
[4]No data at time

TABLE 5
Properties of Two Commercial Composites

| Brand Name | Manufacturer | System Employed | Setting Time | Strength | | | | Color Stability |
|---|---|---|---|---|---|---|---|---|
| | | | | Tensile | | Compressive | | |
| | | | | PSI | MPA | PSI | MPA | |
| Restodent | S. S. White | Powder/Liquid | 2.5 min | 7401.5 ± 870 | 51.0 ± 6.0 | 46985 + 1411 | 324 + 10.1 | |
| Adaptic | Johnson & Johnson | Paste/Paste | 2.0 min | 7021.0 + 377 | 48.4 + 2.6 | 29455.9 + 594 | 203.1 + 4.1 | 3.5-4 |

EXAMPLE V

Synthesis of Para-dimethylaminophenethyl Acetate

The amine of Example I is reacted with acetic anhydride to yield p-dimethylaminophenethyl acetate.

EXAMPLE VI

Synthesis of Methacrylate Ester of Diethylaminophenethanol

Diethylaminophenethanol is synthesized by a procedure analogous to that of Example I. The product is refluxed with methyl methacrylate in the presence of sodium methoxide with removal of methanol to give the corresponding methacrylate ester.

EXAMPLE VII

Synthesis

Aminophenethanol is refluxed in the presence of sodium ethoxide and with removal of ethanol with the compound

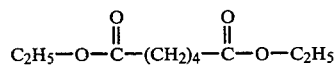

to yield the following intermediate:

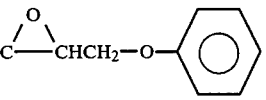

This intermediate is in turn reacted with glycidyl phenyl ether

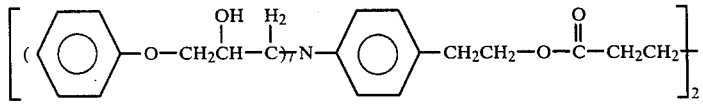

to yield the following final product:

EXAMPLE VIII

Preparation of a Cold-Curing Denture Base Resin

A 0.5% solution of p-(N,N-dimethylamino)phenethanol (see Example I) is dissolved in methyl methacrylate containing 10 ppm methyl ether of hydroquinone. Up to 1% Tinuvin P (Ciba-Geigy), a benzotriazole derivative used as an ultraviolet absorber in polymers, is added. A mixture of one part by weight of this formulation with two parts commercially available powdered, colorless poly(methylmethacrylate) (PMMA) that contains benzoyl peroxide yields within about 12 minutes a polymer that is free of color and is color stable when tested for sunlight stability. For practical use, the colorless PMMA may be replaced by PMMA to which suitable dyes are added in order to achieve shades comparable to those found in human gums and/or palates.

EXAMPLE IX

Preparation of Bone Cement

A 0.5% solution of p-dimethylaminophenethanol (see Example I) is dissolved in methyl methacrylate containing 10 ppm methyl ether of hydroquinone. One part by weight of this formulation is mixed with two parts polymer powder containing 96% poly(methyl methacrylate), 2% polystyrene and 2% benzoyl peroxide. Polymerization occurs shortly after mixing. To increase the polymerization time, additional quantities of a polymerization inhibitor, e.g., butylated hydroxytoluene, may be added.

EXAMPLE X

Synthesis

Para-dimethylaminophenethanol is reacted with succinic anhydride, viz.

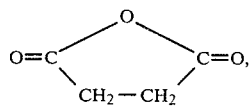

to yield the following product:

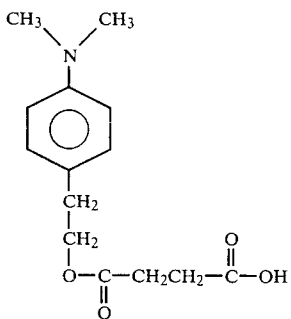

The other tertiary aromatic amines of the present invention may generally be prepared by routes analogous to those detailed in the above Examples, in many instances, by the use of alkyl halides.

The preferred tertiary aromatic amines for use in the present invention include those in which $R_1$ and $R_2$ are normal alkyl substituents with between 1 and 5 carbon atoms, and the reaction products of those in which either $R_1$ or $R_2$ or both are hydrogen with glycidyl phenyl ether or glycidyl methacrylate or the diglycidyl ether of bisphenol A. Because of ease of preparation, those amines with $R_1$ and $R_2$ identical are also preferred. Para-dimethylaminophenethanol is an especially preferred amine.

The amines of the present invention may be formed into a composition of matter comprising the polymerizable monomer and/or curable unsaturated polyester, a peroxide catalyst and a tertiary aromatic amine. In many instances, it will be desirable to further include a reinforcing filler and/or an inhibitor in this composition. Alternatively, a two component system may be prepared composed of a liquid component and a powder component, wherein the liquid component comprises the polymerizable monomer and/or curable unsaturated polyester, tertiary aromatic amine and optional inhibitor, and the powder component comprises the peroxide catalyst and reinforcing filler. The liquid and powder components are combined in order to utilize the composition. The relative quantities of these materials which may be employed vary and may be readily adjusted by one skilled in the art. Representative percentages are indicated in the Examples. For unfilled resins the rate of curing proceeds most rapidly using a molar peroxide to amine ratio between 1.10 and 1.50. For two-component system composites, a much larger molar excess of peroxide is required to obtain optimum hardening time. This much larger excess of peroxide should be expected since only a small portion of the peroxide is accessible to the amine before the composite is cured.

Preferably, the above-described compositions may be employed as restorative dental materials, as cold-curing denture base materials for fabricating or replacing dentures or as orthopedic bone cement. Thus the tertiary aromatic amines of the present invention are employed in a method of treating human teeth (either natural or artificial, as in fixed partial dentures) for filling and for restorative purposes which comprises contacting the teeth with a restorative dental material comprising a polymerizable monomer and/or curable unsaturated polyester, a peroxide catalyst, and a tertiary aromatic amine of specified formula. The amines are employed in a method of fabricating dentures from cold-curing denture base materials in which a composition comprising a polymerizable monomer and/or curable unsaturated polyester, a peroxide catalyst, and a tertiary aromatic amine of specified formula is prepared and polymerized or cured. Representative compositions of monomer and catalyst for denture fabrication are disclosed in R. Phillips, *Skinner's Science of Dental Materials* 193-96, 209, (7th ed. 1973). Similarly, the invention contemplates a method of cementing bone for restorative purposes by analogous means. For this particular use, p-dimethylaminophenethyl acetate is a preferred amine. Representative compositions of monomer and catalyst for orthopedic cements are disclosed in Brauer, Termini & Dickson, 11 *J. Biomed. Mater. Res.*, 577–607 (1977); Haas, Brauer, & Dickson, 57-A *J. Bone & Jt. Surg.* 380–91 (1975). In dental and orthopedic applications, polymerization and/or curing is of necessity a bulk, in situ polymerization with curing at or near room temperature in a period on the order of minutes, preferably within 8 minutes. The compositions containing the tertiary aromatic amines of the present invention satisfy these criteria.

It should be understood that the foregoing disclosure emphasizes certain specific embodiments of the invention and that all modifications or alternatives equivalent thereto are within the spirit or scope of the invention as set forth in the appended claims.

What is claimed is:

1. A composition of matter comprising (1) a component selected from the group consisting of polymerizable vinyl monomers and unsaturated polyesters, (2) a peroxide catalyst, and (3) a tertiary aromatic amine having the following structure:

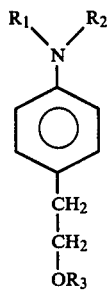  (A)

where $R_1$ and $R_2$ are the same or different and are selected from the following groups:

(a) —$CH_3$, (b) —$CH_2CH_2C_nH_{2n+1}$ with n varying between 0 and 18,

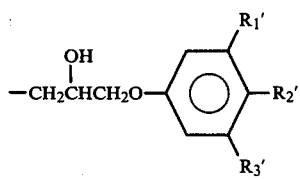  (c)

where $R_1'$, $R_2'$ and $R_3'$ are each either hydrogen, normal alkyl, —$C_nH_{2n+1}$, with n varying between 1 and 20, or t-butyl, but if one $R'$ is t-butyl, then the adjacent $R'$ is hydrogen,

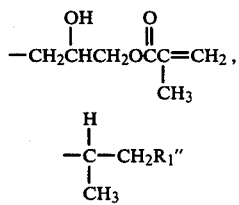  (d)

  (e)

where $R_1''$ is —$C_nH_{2n+1}$ with n varying from 0 to 17, or (f) —$CH_2CH_2OH$;

and where $R_3$ is either hydrogen, or a lower normal alkanoyl group,

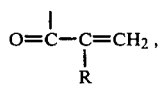

with n varying between 1 and 20, or $$O=\overset{|}{\underset{R}{C}}-C=CH_2,$$

wherein R is hydrogen or a methyl group; or (B) a polymeric amine having 10 or fewer amine groups which is the reaction product of the amine

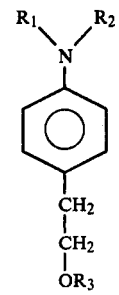

in which $R_1$ and $R_2$ are each hydrogen and $R_3$ is as defined in (A), with the diglycidyl ether of bisphenol A, viz.,

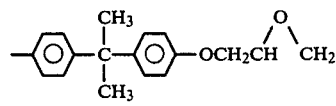

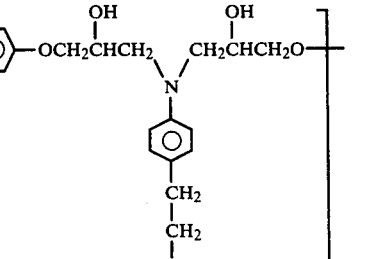

where n varies between 1 and 10, or the hydrolysis product of this polymeric amine, viz.,

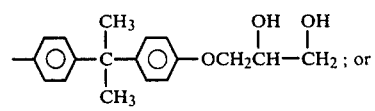

(C) an amine having the formula

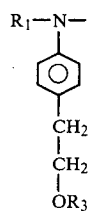

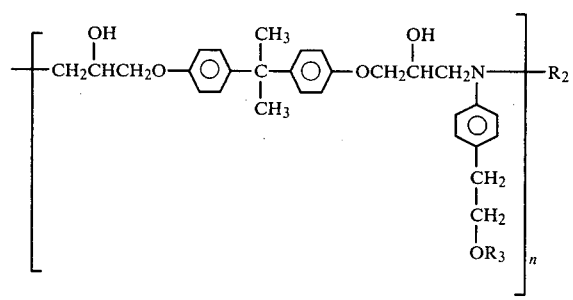

with n varying between 1 and 10, where $R_1$ and $R_2$ are as defined in (A) or are of the formula

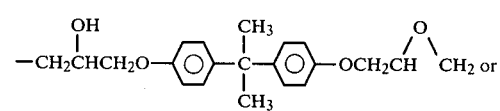 (a)

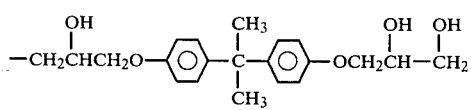 (b)

and where $R_3$ is as defined in (A); or (D) a polymeric amine having 10 or fewer amine groups which is the reaction product of the amine (B) with methacrylic or acrylic acid; or (E) an amine having the formula

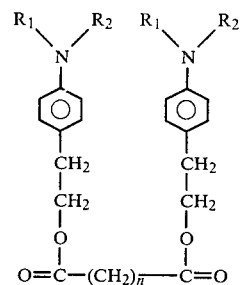

where $R_1$ and $R_2$ are as defined in (A) but with no greater than 5 carbon atoms in the alkyl substituents of $R_1$ and $R_2$, and where n varies between 2 and 10; or (F) an amine having the formula

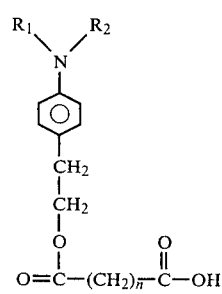

where $R_1$ and $R_2$ are as defined in (A), and where n varies between 2 and 10.

2. A composition of matter as in claim 1 wherein $R_1$ and $R_2$ are the same.

3. A composition of matter as in claim 1(B).

4. A composition of matter as in claim 1 further comprising a reinforcing filler.

5. A composition of matter as in claim 4 wherein the peroxide catalyst is benzoyl peroxide or lauroyl peroxide.

6. A restorative dental material comprising a composition of matter as in claim 1 wherein the component selected from the group consisting of polymerizable vinyl monomers and unsaturated polyesters is a methacrylate ester and the peroxide catalyst is a diacyl peroxide.

7. A restorative dental material as in claim 6 further comprising a reinforcing filler.

8. A bone cement comprising a composition of matter as in claim 1 wherein the peroxide catalyst is a diacyl peroxide.

9. A cold-curing denture base material comprising a composition of matter as in claim 1.

10. A composition of matter as in claims 1, 6, 7, 8 or 9 wherein the tertiary aromatic amine is para-dimethylaminophenethanol.

11. A method of fabricating a cold-curing denture base material which comprises preparing a composition as in claim 1 and permitting it to polymerize or cure.

12. A composition of matter as in claim 3 wherein $R_3$ is hydrogen and n is 2.

* * * * *